(12) United States Patent
Schoenberg

(10) Patent No.: US 6,463,417 B1
(45) Date of Patent: Oct. 8, 2002

(54) METHOD AND SYSTEM FOR DISTRIBUTING HEALTH INFORMATION

(75) Inventor: Roy Schoenberg, Boston, MA (US)

(73) Assignee: CareKey.com, Inc., Boston, MA (US)

(*) Notice: Subject to any disclaimer, the term of this patent is extended or adjusted under 35 U.S.C. 154(b) by 0 days.

(21) Appl. No.: 09/557,724

(22) Filed: Apr. 25, 2000

Related U.S. Application Data (60) Provisional application No. 60/183,857, filed on Feb. 22, 2000.

(51) Int. Cl.$^7$ .............................................. G06F 17/60
(52) U.S. Cl. ................................................. 705/2; 705/3
(58) Field of Search ......................................... 705/2, 3

(56) References Cited

U.S. PATENT DOCUMENTS

| | | | |
|---|---|---|---|
| 4,882,474 A | 11/1989 | Anderi et al. ............... | 235/380 |
| 5,704,044 A | 12/1997 | Tarter et al. ................ | 395/204 |
| 5,805,719 A | 9/1998 | Pare, Jr. et al. ............ | 382/115 |
| 6,076,166 A * | 6/2000 | Moshfeghi et al. ......... | 713/201 |

FOREIGN PATENT DOCUMENTS

WO   WO 01/26020 A1 *   4/2001

OTHER PUBLICATIONS

Bell Atlantic and EMX Team Up to Provide Doctors instant online Access to Medical Data, PR Newswire, Feb. 23, 1999.*

Annas, G., "A National Bill of Patient's Rights", NEJM, 338, p. 695–699, Mar. 5, 1998.

Bakker, A., "Security in Perspective; Luxury or Must?", Int. J. Med. Inf., 49, p. 31–37, 1998.

Baker, D., "PCASSO: Providing Secure Internet Access to Patient Information", www.saic.com.

Barrows, R. Jr. et al., "Privacy, Confidentiality, and Electronic Medical Records", J. Amer. Med. Inf. Assoc., 3, p. 139–148, Mar. 1996.

Cimino, J. et al., "Architecture for a Web–Based Clinical Information System that Keeps the Design Open and the Access Closed", Proc. AMIA Symp., p. 121–125, 1998.

Dudeck, J., "Aspects of Implementing and Harmonizing Healthcare Communication Standards", Int. J. Med. Inf., 48, p. 163–171, Feb. 1998.

(List continued on next page.)

Primary Examiner—Richard Chilcot
Assistant Examiner—J Harle
(74) Attorney, Agent, or Firm—McDermott, Will & Emery (57) ABSTRACT

A method of and system for distributing medical information for an individual over a communications network is disclosed. The method includes the steps of generating a plurality of security access codes, generating a plurality of hierarchical categories, ranging from a low security category to a high security category, categorizing the individual's medical information into privacy levels ranging from a least private level to a most private level, inputting the individual's categorized medical information into the plurality of hierarchical categories, the least private level being input into the low security category and the most private level being input into the high security category and assigning, to each of the categories, one or more of the access security codes, such that the medical information in each category will be released only if the assigned access security codes are received. The method further includes the steps of receiving, from a requestor, one or more of the access security codes over the communications network, determining whether the received access security codes match one or more of the assigned access security codes and transmitting, to the requester over the communications network, the medical information in the categories in which the received security access codes match the assigned security access codes.

35 Claims, 5 Drawing Sheets

OTHER PUBLICATIONS

Epstein, M. et al., "Security for the Digital Information Age of Medicine: Issues, Applications, and Implementation", J. Digit Imaging, 11, p. 33–44, Feb. 1998.

Espinosa, A., "Availability of Health Data: Requirements and Solutions", Int. J. Med. Inf., 49, p. 97–104, Mar. 1998.

Gibby, G. et al., "Availability of Records In an Outpatient Preanesthetic Evaluation Clinic", J. Clin. Mon. & Computing, 14, p. 385–391, Aug. 1998.

Kuilboer, M. et al., "The Availability of Unavailable Information", AMIA Annual Fall Symp., p. 749–753, 1997.

Leape, L., "Error In Medicine", JAMA, 272, p. 1851–1857, Dec. 21, 1994.

Leape, L. et al., "Promotong Patient Safety By Preventing Medical Error", JAMA, 280, p. 1444–1447, Oct. 28, 1998.

Luxenberg, S. et al., "Electronic Forms: Benefits and Drawbacks of a World Wide Web–Based Approach to Data Entry", Proc. AMIA Annual Fall Symp., p. 804–808, 1997.

Mandl, K. et al., "Electronic Patient–Physician Communication: Problems and Promise", Ann. Intern. Med., 129, p. 495–500, Sep. 15, 1998.

Masys, D. et al., "Pateient–Centered Access to Secure Systems Online (PCASSO): A Secure Approach to Clinical Data Access Via the World Wide Web", Proc. AMIA Annual Fall Symp., p. 340–343, 1997.

Auston, I. et al., "Confidentiality of Electronic Health Data: Methods for Protecting Personally Identifiable Information", National Library of Medicine, CBM 95–10, Mar. 1996.

Neame, R., "Smart Cards—The Key to Trustworthy Health Information Systems", BMJ, 314, p. 573–577, Feb. 22, 1997.

Rind, D. et al., "Maintaining the Confidentiality of Medical Records Shared Over the Internet and the World Wide Web", Ann. Inetn. Med., 127, p. 138–141, Jul. 15, 1997.

Schoenberg, R. et al., "Internet Based Repository of Medical Records That Retains Patient Confidentiality", BMJ, 321, p. 1199–1203, Nov. 11, 2000.

Slack, W. et al., "The CCC System in Two Teaching Hospitals: a Progress Report", Int. J. Med. Inf., 54, p. 183–196, Jun. 1999.

Stanberry, B., "The Legal and Ethical Aspects of Telemedicine 1: Confidentiality and the Patient's Rights of Access", J. Telemed. Telecare, 3, p. 179–187, 1997.

Toyoda, K., "Standardization and Security for the EMR", Int. J. Med. Inf., 48, p. 57–60, Feb. 1998.

Woodward, B., "The Computer–Based Patient Record and Confidentiality", NEJM, 333, p. 1419–1422, Nov. 33, 1995.

* cited by examiner

METHOD AND SYSTEM FOR DISTRIBUTING HEALTH INFORMATION

RELATED APPLICATIONS

This application claims the benefit of U.S. Provisional Patent Application No. 60/183,857, filed Feb. 22, 2000.

REFERENCE TO COMPUTER PROGRAM LISTING APPENDIX

The attached compact discs labeled "Copy 1"and "Copy 2", which are identical, are hereby incorporated by reference in their entirety. The discs were created on Jun. 18, 2002 and include a computer program listing named BST99-1295335_1, which is 890KB in size.

FIELD OF THE INVENTION

This invention generally relates to a method of and system for distributing medical information over a communications network, and more specifically to a method of and system for assigning increasing levels of security to portions of an individual's medical records and linking each of the security levels to access security codes that must be supplied by the requester of the medical information in order to access the medical records.

BACKGROUND OF THE INVENTION

When a patient is brought into a hospital for emergency care, it is very unlikely that the patient's medical record will be present in the hospital. A patient's medical record is very important, particularly in an emergency situation, as it typically contains information regarding the patient's blood type, allergies, medical history, etc. Typically, such records are at the location where the patient receives the majority of his or her medical care. In most cases, this is the location of the patient's primary care physician, thus making quick access to the record by the emergency care provider virtually impossible. Furthermore, even if the patient's medical record is accessible, it is likely that much of the information in the record is scattered between several archives in various locations, is obsolete, redundant or indecipherable to the extent that it does not benefit the patient at the point of care.

Presently, the transfer of patient's medical records between care providers is done in a number of different ways. Records can be transferred by phone, facsimile and overnight mail, however, these options are relatively slow, expensive and can be unreliable. The use of email for transferring medical records can be relatively simple and quick. However, email is typically too insecure for transferring the sensitive information contained in a patient's medical record, and information can only be exchanged between parties that are aware of each other's email addresses. Smart cards, which contain memory devices in which a patient's medical data is stored, allow the patient to carry his or her medical records, thereby potentially enabling immediate access to the patient's record. However, the cards are easily lost or misplaced, thus endangering the securing of the record, and smart cards must be compatible with the smart card reader at a particular medical location, which may not always be the case. Furthermore, since the smart card must be physically present at the time the information is needed, remote consultation is impossible. For example, if an ambulance is bringing a patient to the hospital, the information contained in the smart card cannot be accessed by care providers at the hospital until the patient arrives. A further disadvantage of the above methods is that they generally do not permit only selective access to the patient's information, depending on the situation that has precipitated the need for the patient's medical data. For example, if the patient suffers a broken bone, while information regarding the patient's blood type and allergies might be necessary for the proper treatment of the injury, the patient's cardiological or serological data is not. None of the above methods can prevent unnecessary medical data from being divulged to the medical care provider, thus potentially risking the patient's privacy.

While the internet could be used to distribute medical records, there is presently no online system that is capable of securely distributing only the information from a patient's medical record that is necessary for the situation that has required access to the record.

Accordingly, it is an object of this invention to provide a method of and system for distributing medical information in which the medical care provider has quick access to a patient's medical record, but only to the information within the medical record that is necessary for the proper treatment of the patient at that time.

SUMMARY OF THE INVENTION

The present invention is directed to a method of and system for distributing medical information over a communications network. A patient's medical record is divided into a hierarchy of categories, each category having a level of privacy associated therewith which is greater than the previous level. The lowest level category could include information such as blood type and allergies, while a high-level category could include the patient's HIV status. The patient constructs a list of access codes, wherein, the higher the level of the category, the more access codes are required to gain access to the category of the medical record. This enables the patient to control how much access to his or her medical records a particular medical care provider has, by selecting the access codes that are provided to the care provider.

According to the invention, a method for distributing health information includes the steps of generating health data representative of at least one set of health information for an individual, generating access priority data representative of an access priority associated with each of the at least one set of health information, the access priority being based on criteria for release authorization established by the individual, storing at a datastore the health data and associated access priority data and receiving from a requester, by way of a communications network, a request for at least one of the sets of health information, the request including access data correlated to an access priority. The method further includes the steps of processing the access data to determine whether the access data corresponds to the access priority criteria for the requested health information. When the access data corresponds to the access criteria for the requested health information, the requested health information is transmitted to the requestor by way of the communications network, and, when the access data fails to correspond to the access criteria, access to the requestor to the health information is denied. The communications network may be the Internet and the transmitted health information may be encrypted.

According to another embodiment of the invention, a method of distributing medical information for an individual over a communications network includes the steps of generating a plurality of security access codes, generating a plurality of hierarchical categories, ranging from a low security category to a high security category, categorizing the individual's medical information into privacy levels ranging from a least private level to a most private level, inputting the individual's categorized medical information into the plurality of hierarchical categories, the least private level being input into the low security category and the most private level being input into the high security category and assigning, to each of the categories, one or more of the access security codes, such that the medical information in each category will be released only if the assigned access security codes are received. The method further includes the steps of receiving, from a requester, one or more of the access security codes over the communications network, determining whether the received access security codes match one or more of the assigned access security codes and transmitting, to the requestor over the communications network, the medical information in the categories in which the received security access codes match the assigned security access codes.

A system for distributing medical information for an individual over a communications network according to the present invention includes a server system including a computer processor and associated memory, the server system having database of a plurality or hierarchical categories for the individual, the categories ranging from a low security category to a high security category, each of the categories having medical information of the information contained therein. The medical information ranges from least private information to most private information, the least private medical information being contained in the low security category and the most private medical information being contained in the high security category. Each of the categories have one or more security access codes assigned thereto. The system further includes a request system including a computer processor and associated memory, the requestor system inputting one or more of the security access codes to the server system over the communications network and an access determining device for transmitting, to the requester system, the medical information in each of the categories in which the input security access codes match the assigned security access codes. The system may further include a setup system, having a computer processor and associated memory, for inputting the medical information to the database. The security access codes may be defined by a user and assigned to the categories by the user through the setup system. More of the security access codes may be required to access the high security categories than the low security categories. The setup system and the requester system may be the same system. The setup system may be coupleable to said network by a wired or a wireless connection, and may be a personal computer, an interactive television system, a personal digital assistant or a cellular telephone.

BRIEF DESCRIPTION OF THE DRAWINGS

The foregoing and other objects of this invention, the various features thereof, as well as the invention itself may be more fully understood from the following description when read together with the accompanying drawings in which.

DETAILED DESCRIPTION OF THE PREFERRED EMBODIMENTS

Figure 1:
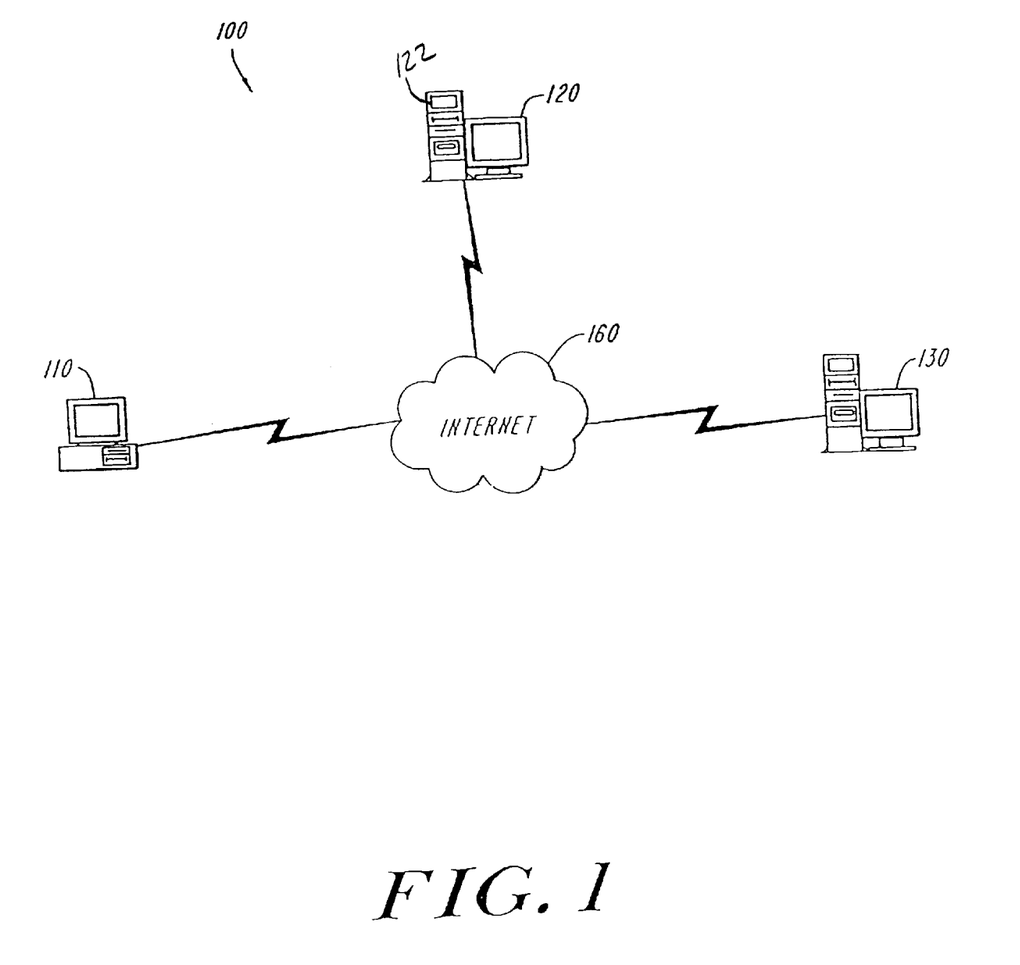
FIG. 1 is a diagrammatic view of a system for distributing medical information in accordance with the present invention.

The present invention enables a medical care provider to have remote access to a patient's medical record, while also enabling the patient to dictate exactly how much information the medical care provider can access. FIG. 1 shows a diagram of a system 100 for distributing medical information in accordance with a preferred embodiment of the present invention. The system 100 includes setup system 110, server system 120 and request system 130 all connected to a common communications network 160. Preferably, the setup system 110, server system 120 and request system 130 can each be a personal computer such as an IBM PC or IBM PC compatible system or an APPLE® MacINTOSH® system or a more advanced computer system such as an Alpha-based computer system available from Compaq Computer Corporation or SPARC® Station computer system available from SUN Microsystems Corporation, although a main frame computer system can also be used. Preferably, the communications channel 160 is a TCP/IP-based network such as the Internet or an intranet, although almost any well known LAN, WAN or VPN technology can be used.

In one preferred embodiment of the invention, the setup system 110 and request system 130 are IBM PC compatible systems operating a Microsoft Windows® operating system and server system 120 is configured as a web server providing access to information such as web pages in HTML format via the HyperText Transport Protocol (http). The setup system 110 and request system 130 include software to allow viewing of web pages, commonly referred to as a web browser, thus being capable of accessing web pages located on server system 120. Furthermore, setup system 110, server system 120 and request system 130 include software for encrypting and decrypting data that is transmitted over the communications network 160. Alternatively, setup system 110 and request system 130 can be any wired or wireless device that can be connected to a communications network, such as an interactive television system, such as WEBTV, a personal digital assistant (PDA) or a cellular telephone. In this preferred embodiment, setup system 110 is located at the patient's primary care physician's office and request system 130 is located wherever access to a patient's medical record is required, such as in an emergency room, ambulance or another doctor's office.

Figure 2:
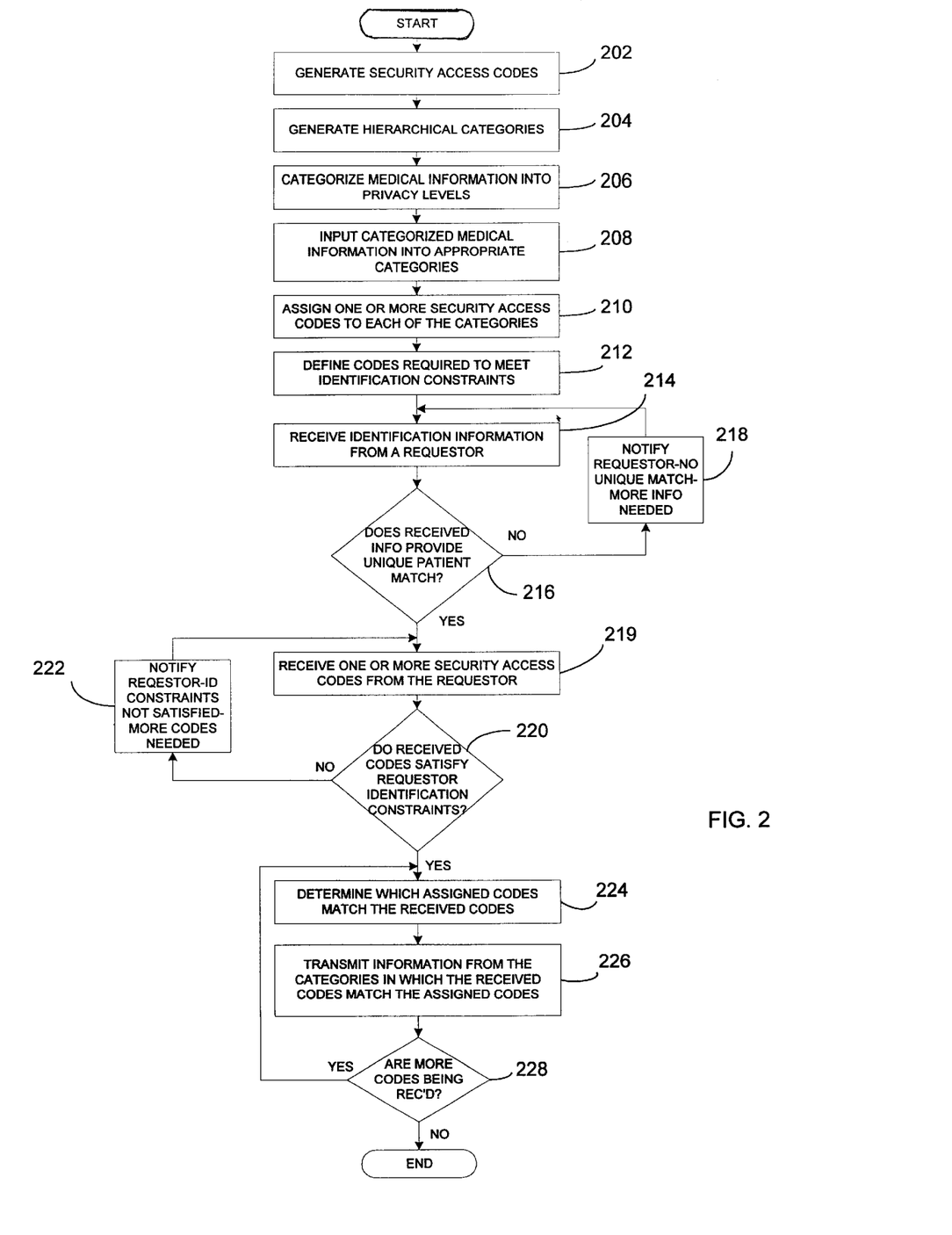
FIG. 2 is a flow diagram of a method of distributing medical information in accordance with the present invention.

FIG. 2 shows a flow diagram of the method of distributing medical information according to the present invention. First, the user of the setup system 110, FIG. 1, who can be the patient or the patient's physician, generates security access codes, step 202, which will provide varying access to the patient's medical records. Such security access codes can include demographic data such as the patient's name, birth date, social security number, address and phone number; non-demographic data such as a passport number and the patient's native language; physical attributes such as eye and hair color and scars or other identifying marks; and user-definable fields such as passwords. The user then generates hierarchical categories into which the patient's medical information will be stored, step 204. These categories range from a low security category, for information that the patient is less concerned about becoming known by a third party, to a high security category, for information that the patient is more concerned about becoming known by a third party. The patient and/or the patient's physician then determine the level of privacy that is desired for each piece of medical information in the patient's medical record, step 206. The least private level could include information such as the patient's blood type and allergies. The most private level could include HIV data. Intermediate levels of privacy may include serology data, psychiatric data, cardiology data and genetic data. After the levels of privacy for each piece of the patient's medical information is determined, the information is transmitted from the setup system 110, FIG. 1, to the server system 120 over the communications network 160, and is stored in a database 122 of the server system 120, step 208. The patient then assigns one or more of the security access codes to each of the categories in the database 122, step 210. Preferably, security access codes that are easier to ascertain are assigned to low security categories, while security access codes that are more difficult to ascertain are assigned to high security categories. This allows the patient to more precisely control who has access to the categories, by enabling the patient to provide the security access codes for each of the categories only to medical personnel who have a "need-to-know" the particular information in each category.

As a further security measure, the patient can define which of the security access codes are necessary to be input by the requester to identify the requestor as being authorized to access the patient's medical record, step 212. The security access code that will identify an authorized requester is preferably a code that will not be easily guessed by an unauthorized requester.

When a patient's medical record is needed, the requester inputs to the server system 120, FIG. 1, through request system 130 and over network 160, any information that is known about the patient in order to identify the patient. While prior art systems require specific predetermined data to identify a patient, the present invention is capable of searching its database to identify the patient based on whatever information the requester can provide. Such information can include, but is not limited to, actual medical record numbers for a particular hospital, demographic data such as the patient's name, age and sex, information from a smart card that identifies the patient, retinal or iris scans and fingerprints. This flexible identification system enables the present invention to be used in conjunction with existing legacy systems. Since the database 122 may include medical records for a great number of patient's, the server system 120 determines whether, based on the identification information input by the requestor, a unique patient match has been achieved, step 216. In this embodiment, the identification information input by the requester could also be the security access codes set up by the patient. If the identification information input by the requester does not define a unique patient in the database, the server system notifies the requester that more identification information is needed to establish a unique patient match, step 218. If the identification information provided by the requester provides a unique patient match, step 216, the server system prompts the requester to enter security access codes for the patient. The server system then receives one or more of the security access codes input to the server system by the requester, step 219. The server system 120 determines whether the received security access codes satisfy the requester identification constraints, step 220. If they do not, the system notifies the requester that the identification constraints have not been satisfied, step 222. If the identification constraints have been satisfied, the server system determines which of the assigned access codes match the received access codes input by the requester, step 224, and transmits, to the request system 130 over the network 160, the information from the categories in which the received security access codes match the assigned security access codes, step 226. If more of the security access codes are received from the requestor, step 228, the system returns to step 224 to determine which of the assigned codes match the received codes. If no more codes are received in step 228, the process is terminated.

Figure 3:
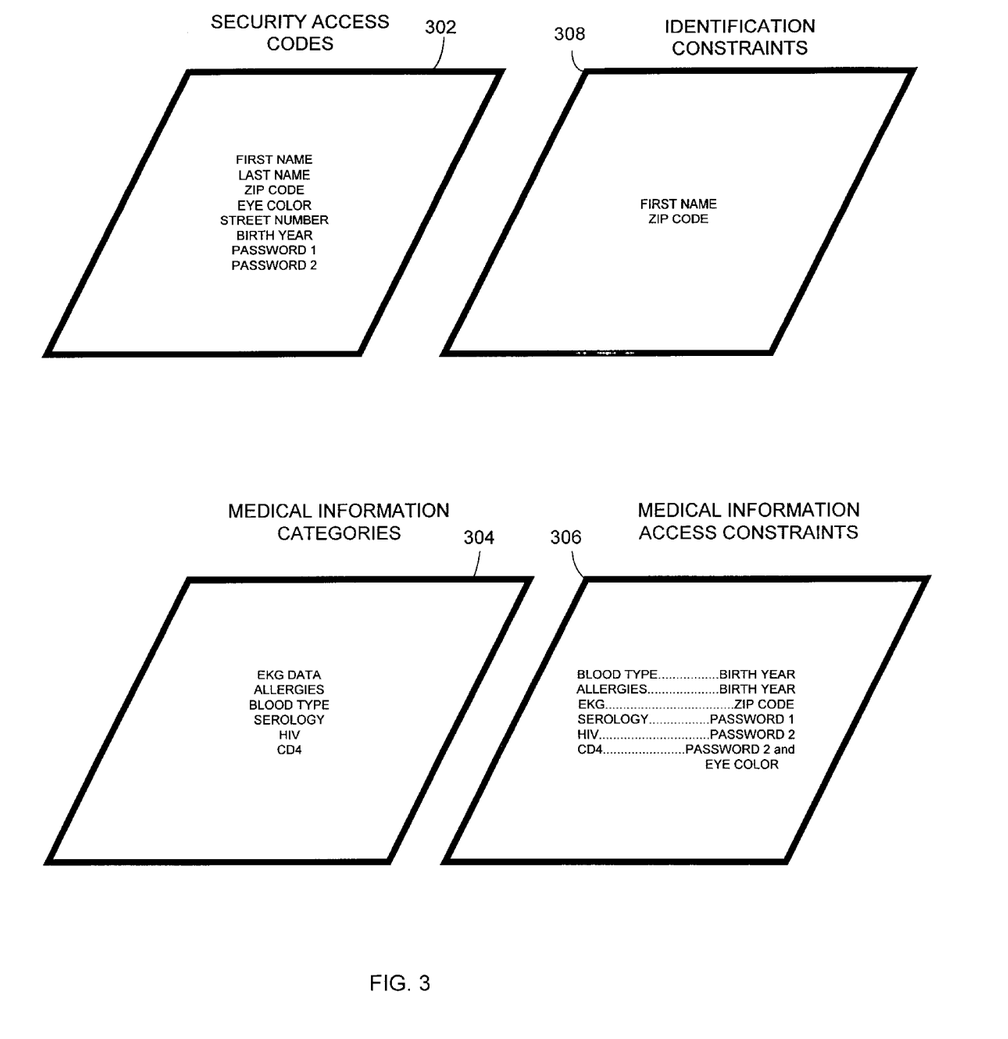
FIG. 3 is a schematic diagram of an example medical record in accordance with the system of FIG. 1.

An example of the above method will now be described with reference to FIG. 3, which is a schematic diagram of a patient's medical record in accordance to the present invention. Shown at 302 are the security access codes generated by the patient in step 202, FIG. 2. In this example, the security access codes are the patient's first and last name, zip code, eye color, street number, birth year and two passwords. Shown at 304 are the medical information categories generated by the patient in step 204. These categories include EKG data, allergies, blood type, serology, HIV and CD4. Shown at 306 are the security access codes that are assigned to the categories in step 210. As described above, security access codes that are easily ascertained are assigned to low security categories and security access codes that are more difficult to ascertain are assigned to high security categories. In this example, the patient's birth year is assigned to the blood type and allergies, while the patient-defined passwords are assigned to the HIV and CD4 categories. In step 212, the patient's first name and zip code, block 308, are chosen by the patient as the identification constraints that must be input by the requester to establish that he or she is authorized to access the patient's record. The following table shows the response of the system of the present invention to various combinations of security access codes received from the requestor:

| If Requestor supplies this data | System will respond with |
| --- | --- |
| A. First Name | "More than one patient found, No unique match" |
| B. First Name, Birth Year, Key 1 | "Unique Match, ID constraints not satisfied" |
| C. First Name, Zip Code, Birth Year | EKG data, Allergies, Blood Type |
| D. First Name, Zip Code, Birth Year, Password 1 | EKG data, Allergies, Blood Type, Serology, |
| E. First Name, Zip Code, Birth Year, Password 1, Password 2 | EKG data, Allergies, Blood Type, Serology, HIV |
| F. First Name, Zip Code, Birth Year, Password 1, Password 2, Eye Color | EKG data, Allergies, Blood Type, Serology, HIV, CD4 |

In case A, because only the first name of the patient has been received, the system determines that a unique patient match has not been found, step 216, and notifies the requester that more identification information is needed, step 218. In case B, the first name, birth year and password 1 are received, step 214. Although these codes allow the system to identify the patient, step 216, the identification constraints (the first name and zip code) have not been satisfied, step 220. The system then notifies the requestor that more security access codes are needed to satisfy the identification constraints, step 222. In case C, the first name, zip code and birth year are received, step 214. A unique patient match is found, step 216 and the identification constraints are satisfied, step 220. The system then determines which of the assigned security access codes match the received security access codes, step 224, and transmits the information in the matched categories to the requestor over the communications network, step 226. In case C, because the zip code and birth year are received, referring to block 306, FIG. 3, the EKG data, allergy information and blood type are transmitted from the database to the requestor. In case D, in addition to the first name zip code and birth year, password 1 is received, step 228. Accordingly, in addition to the information transmitted in case C, the patient's serology information is transmitted to the requester. In case E, with the receipt of password 2, the patient's HIV data is transmitted and, in case F, the receipt of password 2 and the patient's eye color prompts the transmission of the patient's CD4 data, in addition to all of the information transmitted in the previous cases.

Figure 4:
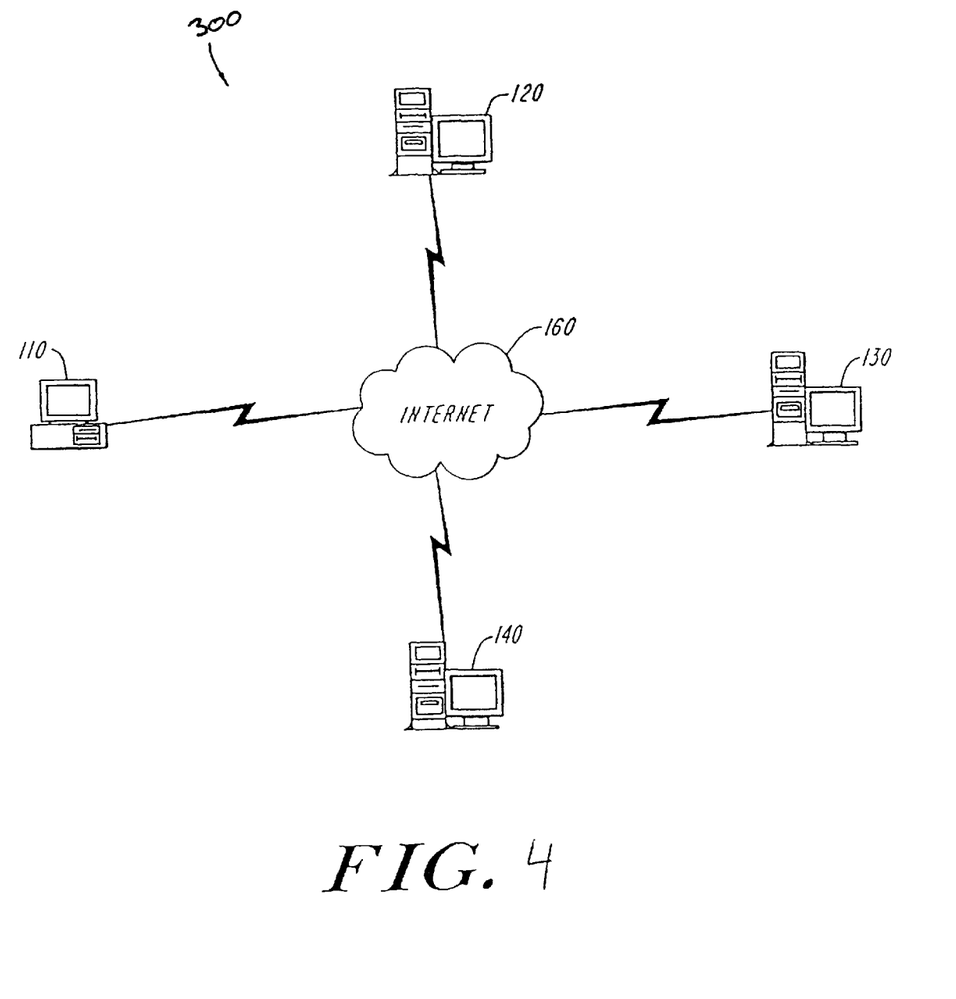
FIG. 4 is a diagrammatic view of another embodiment of the system of FIG. 1.

While the invention has been described as including one setup system that accesses the server system, a plurality of setup systems may be coupled to the server system in order to allow patients at different locations to access the server system. Such a configuration is illustrated in FIG. 4. In this system 300, in addition to the setup system 110, a second server system 140 is coupleable to the server system 120 over communications network 160 for the purpose distributing medical information in the manner described above. It will be understood that the server system can be accessed through any number of setup systems, and that any number of request systems may access the server system in the manner described above.

Figure 5:
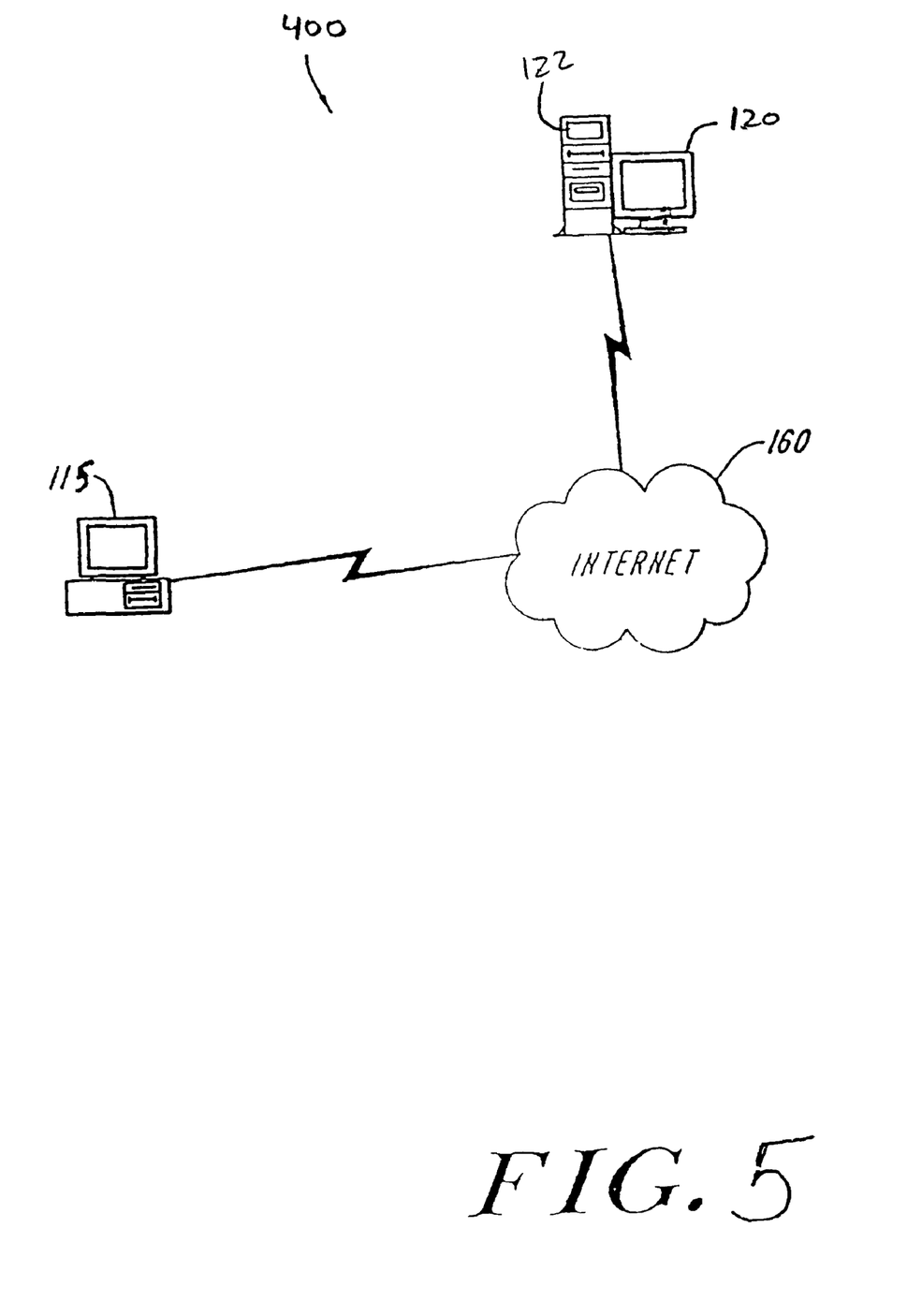
FIG. 5 is a diagrammatic view of yet another embodiment of the system of FIG. 1.

In another embodiment, shown at 400 in FIG. 5, system 115 can be used both as the setup system, for setting up the patient's medical record on the database 122 of server system as described above, and as the request system for inputting security access codes and receiving medical information from the database 122 of the server system 120, as described above.

Accordingly, the present invention provides a method of and system for distributing medical information over a network in a granular manner, in which the patient determines the level of security associated with each category of his or her medical record. A requester of the patient's medical information must input the proper security access codes to the system in order to obtain the information contained within the record. The system enables the patient to distribute the security access codes for the hierarchy of security categories to medical personnel on a "need-to-know" basis, thus reducing the risk that highly private medical information be exposed to unauthorized personnel.

Attached as Appendix A is the Javascript and VBscript code used to implement the present invention and a sample database on which the invention can be used.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of distributing health information, comprising the steps of:

A. categorizing health information for an individual into a plurality of hierarchical sets of health information;

B. assigning by said individual access priority data representative of an access priority level to each of said plurality of sets of health information in said hierarchy, said access priority levels being based on differing criteria for release authorization for each of said plurality of sets of health information established by said individual;

C. storing, at a datastore, each of said plurality of sets of health information in said hierarchy and associated access priority data;

D. providing, by said individual to one or more requesters, access priority data corresponding to a desired level in said hierarchy;

E. receiving, from a requestor, by way of a communications network, a request for at least one of said plurality of sets of health information in said hierarchy, said request including access priority data correlated to an access priority level;

F. processing said access priority data to determine whether said access priority data corresponds to said access priority level for said requested health information; and i. when said access priority data corresponds to said access priority level for said requested health information, transmitting said requested health information to said requester by way of said communications network, and ii. when said access data fails to correspond to said access priority level, denying access to said requestor to said health information.

2. The method according to claim 1, wherein said communications network is the Internet.

3. The method according to claim 1, wherein said transmitted health information is encrypted.

4. The method of distributing medical according to claim 2 further comprising the step of designating certain of said access priority data as identification constraints which must be received in step D before access to said medical information is granted.

5. A method of distributing medical information for an individual over a communications network comprising the steps of:

A. generating a plurality of access security codes;

B. generating a plurality of hierarchical categories, ranging from a low security category to a high security category;

C. categorizing the individual's medical information into privacy levels ranging from a least private level to a most private level;

D. inputting the individual's categorized medical information into said plurality of hierarchical categories, said least private level being input into said low security category and said most private level being input into said high security category;

E. assigning by said individual, to each of said categories, one or more of said access security codes, such that said medical information in each category will be released only if the assigned access security codes are received;

F. providing, by said individual to one or more requestors, access priority data corresponding to a desired level in said hierarchy;

G. receiving, from a requestor, one or more of said access security codes over said communications network;

H. determining whether said received access security codes match one or more of said assigned access security codes; and I. transmitting, to said requestor over said communications network, said medical information in said categories in which said received security access codes match said assigned security access codes.

6. The method of distributing medical information for an individual over a network according to claim 5, wherein said communications network is the internet.

7. The method of distributing medical information for an individual over a network according to claim 6, wherein said released medical information is encrypted.

8. The method of distributing medical information for an individual over a network according to claim 6 further comprising the step of designating certain of said security access codes as identification constraints which must be received in step F before access to said medical information is granted.

9. The method of distributing medical information for an individual over a network according to claim 6 wherein, prior to step F, identification information is received from the requestor, said identification information being for identifying the individual.

10. The method of distributing medical information for an individual over a network according to claim 9 wherein said identification information is selected from the group consisting of the individual's medical record numbers, demographic data, information from a smart card that identifies the patient, retinal scans, iris scans and fingerprints.

11. The method of distributing medical information for an individual over a network according to claim 9 wherein said identification information is any information about the individual which is available to said requester.

12. A system for distributing medical information for an individual over a communications network comprising:

a server system including a computer processor and associated memory, said server system having database of a plurality of hierarchical categories for the individual, said categories ranging from a low security category to a high security category, each of said categories having medical information of said individual contained therein, said medical information ranging from least private information to most private information, said least private medical information being contained in said low security category and said most private medical information being contained in said high security category, each of said categories having one or more security access codes assigned thereto;

a request system including a computer processor and associated memory, said request system inputting, in response to a requestor, one or more of said security access codes provided to said requestor by said individual, to said server system over said communications network; and an access determining device for transmitting, to said request system, the medical information in each of said categories in which said input security access codes match said assigned security access codes.

13. The system according to claim 12 wherein said communications network is the internet.

14. The system according to claim 13, further including a setup system, including a computer processor and associated memory, for inputting said medical information to said database.

15. The system according to claim 14 wherein said security access codes are defined by a user and are assigned to said categories by said user through said setup system.

16. The system according to claim 13 wherein more of said security access codes are required to access said high security categories than said low security categories.

17. The system according to claim 13 wherein said setup system and said requester system are the same system.

18. The system of claim 13 wherein said request system is coupleable to said network by wired connection.

19. The system of claim 18 wherein said request system is selected from the group consisting of a personal computer, an interactive television system, a personal digital assistant and a cellular telephone.

20. The system of claim 13 wherein said request system is coupleable to said network by a wireless connection.

21. The system of claim 20 wherein said request system is selected from the group consisting of a personal computer, an interactive television system, a personal digital assistant and a cellular telephone.

22. The system of claim 14 wherein said setup system is coupleable to said network by a wired connection.

23. The system of claim 22 wherein said setup system is selected from the group consisting of a personal computer, an interactive television system, a personal digital assistant and a cellular telephone.

24. The system of claim 14 wherein said setup system is coupleable to said network by a wireless connection.

25. The system of claim 24 wherein said setup system is selected from the group consisting of a personal computer, an interactive television system, a personal digital assistant and a cellular telephone.

26. A method of distributing personal information, comprising the steps of:

A. categorizing personal information for an individual into a plurality of hierarchical sets of personal information;

B. assigning, by said individual, access priority data representative of an access priority level to each of said plurality of sets of personal information in said hierarchy, said access priority levels being based on differing criteria for release authorization for each of said plurality of sets of personal information established by said individual;

C. storing, at a datastore, each of said plurality of sets of personal information in said hierarchy and associated access priority data;

D. providing, by said individual to one or more requesters, access priority data corresponding to a desired level in said hierarchy;

E. receiving from a requestor, by way of a communications network, a request for at least one of said plurality of sets of personal information in said hierarchy, said request including access priority data correlated to an access priority level;

F. processing said access priority data to determine whether said access priority data corresponds to said access priority level for said requested personal information; and i. when said access priority data corresponds to said access priority level for said requested personal information, transmitting said requested personal information to said requestor by way of said communications network, and ii. when said access data fails to correspond to said access priority level, denying access to said requester to said personal information.

27. A method of distributing personal information for an individual over a communications network comprising the steps of:

A. generating a plurality of access security codes;

B. generating a plurality of hierarchical categories, ranging from a low security category to a high security category;

C. categorizing the individual's personal information into privacy levels ranging from a least private level to a most private level;

D. inputting the individual's categorized personal information into said plurality of hierarchical categories, said least private level being input into said low security category and said most private level being input into said high security category;

E. assigning, by said individual, to each of said categories, one or more of said access security codes, such that said personal information in each category will be released only if the assigned access security codes are received;

F. providing by said individual to one or more requestors, access priority data corresponding to a desired level in said hierarchy;

G. receiving, from a requestor, one or more of said access security codes over said communications network;

H. determining whether said received access security codes match one or more of said assigned access security codes; and I. transmitting, to said requestor over said communications network, said personal information in said categories in said hierarchy which said received security access codes match said assigned security access codes.

28. The method of distributing personal information for an individual over a network according to claim 27 further comprising the step of designating certain of said security access codes as identification constraints which must be received in step F before access to said personal information is granted.

29. The method of distributing personal information for an individual over a network according to claim 28 wherein, prior to step F, identification information is received from the requester, said identification information being for identifying the individual.

30. The method of distributing personal information for an individual over a network according to claim 29 wherein said identification information is selected from the group consisting of the individual's demographic data, information from a smart card that identifies the patient, retinal scans, iris scans and fingerprints.

31. A system for distributing personal information for an individual over a communications network comprising:

a server system including a computer processor and associated memory, said server system having database of a plurality of hierarchical categories for the individual, said categories ranging from a low security category to a high security category, each of said categories having personal information of said individual contained therein, said personal information ranging from least private information to most private information, said least private personal information being contained in said low security category and said most private personal information being contained in said high security category, each of said categories having one or more security access codes assigned thereto;

a request system including a computer processor and associated memory, said request system inputting, in response to a requester, one or more of said security access codes provided to said requester by said individual, to said server system over said communications network; and an access determining device for transmitting, to said requests system, the personal information in each of said categories in which said input security access codes match said assigned security access codes.

32. The system according to claim 31, further including a setup system, including a computer processor and associated memory, for inputting said personal information to said database.

33. The system according to claim 32 wherein said security access codes are defined by said individual and are assigned to said categories by said individual through said setup system.

34. The system according to claim 31 wherein more of said security access codes are required to access said high security categories than said low security categories.

35. The system according to claim 32 wherein said setup system and said request system are the same system.

* * * * *